US008835656B2

(12) United States Patent
Tsukamoto et al.

(10) Patent No.: US 8,835,656 B2
(45) Date of Patent: Sep. 16, 2014

(54) LINKER AND SUPPORT FOR SOLID PHASE SYNTHESIS OF NUCLEIC ACID (71) Applicants: Nitto Denko Corporation, Ibaraki (JP); National University Corporation Nagoya University, Nagoya (JP)

(72) Inventors: Masaki Tsukamoto, Nagoya (JP); Noritaka Suzuki, Toyota (JP); Yoshihiro Hayakawa, Ichinomiya (JP); Eri Maeta, Ibaraki (JP); Kenjiro Mori, Ibaraki (JP); Kenjiro Minomi, Ibaraki (JP)

(73) Assignees: Nitto Denko Corporation, Ibaraki (JP); National University Corporation Nagoya University, Nagoya (JP)

( * ) Notice: Subject to any disclaimer, the term of this patent is extended or adjusted under 35 U.S.C. 154(b) by 81 days.

(21) Appl. No.: 13/754,055

(22) Filed: Jan. 30, 2013

(65) Prior Publication Data
US 2013/0197117 A1  Aug. 1, 2013

(30) Foreign Application Priority Data

Jan. 30, 2012  (JP) .................. 2012-016895

(51) Int. Cl.
*C07D 493/22* (2006.01)
*C07H 21/04* (2006.01)

(52) U.S. Cl.
CPC .............. *C07D 493/22* (2013.01); *C07H 21/04* (2013.01)
USPC ........... 549/457; 549/214; 521/146; 521/149; 536/23.1

(58) Field of Classification Search
CPC ........ C08D 93/22; C07H 21/04; C40B 80/00; C40B 50/18
See application file for complete search history.

(56) References Cited

U.S. PATENT DOCUMENTS 5,681,945 A  10/1997  McLean et al.

6,653,468 B1  11/2003  Guzaev et al.
(Continued)

FOREIGN PATENT DOCUMENTS

WO  WO 2004/058794 A1  7/2004
WO  WO 2005/049621 A1  6/2005

OTHER PUBLICATIONS

Sera, A.; Ohara, M.; Kubo, T.; Itoh, K.; Yamada, H.; Mikata, Y. "High Pressure Mediated Diels-Alder Reaction of Furan with Dialkyl (Acetoxymethylene)malonate" J. Org. Chem. 1988, 53, 5460-5464.*

(Continued)

*Primary Examiner* — Randy Gulakowski
*Assistant Examiner* — Christina Wales
(74) *Attorney, Agent, or Firm* — Leydig, Voit & Mayer, Ltd.

(57) ABSTRACT

The invention provides a universal linker capable of synthesizing nucleic acid having a hydroxy group at the 3' terminal, a universal support carrying the linker, and a synthesis method of nucleic acid using the universal support. The linker contains a compound represented by the formula

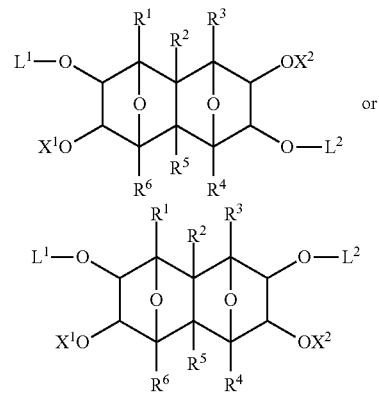

or wherein each symbol is as defined in the specification.

20 Claims, 3 Drawing Sheets

(56) References Cited

U.S. PATENT DOCUMENTS

| | | | |
|---|---|---|---|
| 7,772,439 B2* | 8/2010 | Weiss et al. | 568/15 |
| 7,786,296 B2* | 8/2010 | Sekine et al. | 536/28.1 |
| 8,669,356 B2* | 3/2014 | Hayakawa et al. | 536/25.3 |
| 2005/0182241 A1 | 8/2005 | Ngo et al. | |
| 2010/0239509 A1* | 9/2010 | Chodorowski-Kimmes et al. | 424/59 |

OTHER PUBLICATIONS

European Patent Office, Extended European Search Report for European Patent Application 13153107.1 (Apr. 29, 2013).

Azhayev et al., *Tetrahedron*, 57: 4977-4986 (2001).

Beaucage, Serge L., *Current Protocols in Nucleic Acid Chemistry*, 3.0.1-3.0.3 (2000).

Nelson et al., *BioTechniques*, 22(4): 752-756 (1997).

Pon, Richard T., *Current Protocols in Nucleic Acid Chemistry*, 3.1.1-3.1.28 (2000).

Ravikumar et al., *Organic Process Research & Development*, 12(3): 399-410 (2008).

\* cited by examiner

LINKER AND SUPPORT FOR SOLID PHASE SYNTHESIS OF NUCLEIC ACID

CROSS-REFERENCE TO RELATED APPLICATIONS

This patent application claims the benefit of Japanese Patent Application No. 2012-016895, filed Jan. 30, 2012, which is incorporated by reference in its entirety herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 446 bytes ASCII (Text) file named "712172SequenceListing.txt," created Jan. 30, 2013.

TECHNICAL FIELD OF THE INVENTION

The present invention relates to a linker to be used for solid phase synthesis of nucleic acid, a support for solid phase synthesis carrying the linker, and a production method of nucleic acid using the support.

BACKGROUND OF THE INVENTION

For chemical synthesis of nucleic acid such as DNA, RNA and the like, a solid phase synthesis process using a phosphoramidite method is widely employed. In the solid phase phosphoramidite method, nucleic acid is generally synthesized by the following steps.

First, nucleoside to be the 3' terminal of the nucleic acid to be synthesized is ester bonded to a cleaving linker such as succinyl group and the like via 3'-OH group so that the nucleoside is previously carried on a support for solid phase synthesis (nucleoside linker). Then, the support for solid phase synthesis on which the nucleoside linker is carried is placed in a reaction column which is then set on an automated nucleic acid synthesizer.

Thereafter, a synthesis reaction comprising the following steps is generally performed in the reaction column according to a synthesis program of the automated nucleic acid synthesizer:
(1) a step of deprotection of 5'-OH group of the protected nucleoside with an acid such as trichloroacetic acid/dichloromethane solution and the like;
(2) a step of coupling nucleosidephosphoramidite (nucleic acid monomer) with the deprotected 5'-OH group in the presence of an activator (tetrazole etc.);
(3) a step of capping an unreacted 5'-OH group with acetic anhydride and the like; and
(4) a step of oxidizing phosphite with aqueous iodine and the like.

By repeating the synthesis cycle, an elongation reaction of oligonucleotide from the 3' terminal to the 5' terminal direction is promoted, and a nucleic acid having a desired sequence is synthesized.

Lastly, a cleaving linker is hydrolyzed with aqueous ammonia, methylamine solution and the like to cleave the synthesized nucleic acid from the support for solid phase synthesis (non-patent document 1).

When the above-mentioned synthesis is performed, as mentioned above, it is necessary to carry, in advance, nucleoside to be the 3' terminal (starting material) on a support for solid phase synthesis via a cleaving linker. Moreover, the 3' terminal varies depending on the sequence of nucleic acid desired to be synthesized. In the case of DNA oligonucleotide, 4 kinds of dA, dG, dC, dT are necessary, and in the case of RNA, 4 kinds of rA, rG, rC, rU are also necessary. For synthesis of modified oligonucleotide, a support for solid phase synthesis previously carrying a modified nucleoside is necessary, making the process complicated.

To solve the aforementioned problems, a support for solid phase synthesis carrying a universal linker (universal support) has been developed as a linker to connect a solid phase support and a starting material, in the place of nucleoside.succinyl linker and the like generally used heretofore. Using the universal support, the process includes, irrespective of the kind of nucleoside or nucleotide for the 3' terminal of nucleic acid desired to be synthesized, reacting nucleoside phospho.ramidite to be the 3' terminal in the same step as general automated nucleic acid synthesis to start the synthesis and, after synthesizing the desired nucleic acid, cleaving the nucleic acid from the support for solid phase synthesis by a method similar to a general method. It is not necessary to prepare a support for solid phase synthesis carrying various nucleoside-linkers as mentioned above.

There are proposed some universal supports, which render the 3' terminal of the nucleic acid desired to be synthesized a hydroxy group (patent documents 1-4 and non-patent documents 2 and 3). The structure of these universal supports has two adjacent carbon atoms, one carbon atom being bound with —OH group to be the starting point of nucleic acid synthesis, and the other carbon atom being bound with a group (e.g., —OH group, —NH$_2$ group, —SH group) to be a nucleophilic group upon removal of the protecting group. When the nucleic acid is cleaved by aqueous ammonia and the like after the nucleic acid synthesis, the protecting groups of these nucleophilic groups are also dissociated to attack the 3' terminal phosphorus, and the phosphate group is cleaved from the 3' terminal to form cyclic phosphate ester. All are used to synthesize nucleic acid having a hydroxy group at the 3' terminal.

A nucleic acid having a hydroxy group at the 3' terminal is highly useful since it is widely demanded in the biochemical field, such as a nucleic acid medicine and the like. In view of such situation, a universal linker capable of synthesizing a nucleic acid having a hydroxy group at the 5' terminal or 3' terminal, and a universal support carrying the linker are desired.

DOCUMENT LIST

Patent Documents patent document 1: U.S. Pat. No. 5,681,945
patent document 2: U.S. Pat. No. 6,653,468
patent document 3: WO2005/049621
patent document 4: US-A-2005/0182241

Non-Patent Documents non-patent document 1: Current Protocols in Nucleic Acid Chemistry (2000) 3.1.1-3.1.28
non-patent document 2: Bio Techniques, 22, 752-756 (1997)
non-patent document 3: Tetrahedron, 57, 4977-4986 (2001)

SUMMARY OF THE INVENTION

Problems to be Solved by the Invention

The present invention aims to provide a universal linker capable of synthesizing a nucleic acid having a hydroxy group at the 3' terminal, a universal support carrying the linker, and a method for synthesizing a nucleic acid using the universal support.

Particularly, the present invention aims to provide a support for solid phase synthesis, which is capable of universally synthesizing a nucleic acid having a hydroxy group at the 3' terminal in a high purity, which does not require a support for solid phase synthesis with modified nucleoside carried in advance even when synthesizing a modified oligonucleotide.

Means of Solving the Problems

Accordingly, the present invention provides the following.
[1] A linker for nucleic acid solid phase synthesis, comprising a compound represented by the following formula wherein
$X^1$ and $X^2$ are each independently a hydroxy-protecting group that is dissociated by acid,
$L^1$ and $L^2$ are each independently a linkage moiety that is cleaved by alkali,
$R^1$-$R^6$ are each independently a hydrogen atom; a $C_{1-6}$ alkyl group optionally substituted by a $C_{1-6}$ alkoxy group; a $C_{1-6}$ alkoxy group; a $C_{1-7}$ acyl group; a mono or di-$C_{1-6}$ alkylamino group; or a halogen atom, or
$R^2$ and $R^5$ are joined to form, together with the carbon atom bonded thereto, a 3- to 8-membered carbocycle or heterocycle each optionally substituted by a substituent selected from (1) an oxo group, (2) a $C_{1-6}$ alkyl group optionally substituted by a $C_{1-6}$ alkoxy group, and (3) a phenyl group optionally substituted by a $C_{1-6}$ alkoxy-carbonyl group.
[2] The linker of the above-mentioned [1], wherein at least one of $L^1$ and $L^2$ can be linked to a support for nucleic acid solid phase synthesis.
[3] The linker of the above-mentioned [1] or [2], wherein $X^1$ and $X^2$ are dimethoxytrityl groups.
[4] A support for nucleic acid solid phase synthesis, which has a structure represented by the following formula -continued wherein
$X^1$ and $X^2$ are each independently a hydroxy-protecting group that is dissociated by acid,
$L^1$ and $L^2$ are each independently a linkage moiety that is cleaved by alkali,
Sp is a solid phase support,
$R^1$-$R^6$ are each independently a hydrogen atom; a $C_{1-6}$ alkyl group optionally substituted by a $C_{1-6}$ alkoxy group; a $C_{1-6}$ alkoxy group; a $C_{1-7}$ acyl group; a mono or di-$C_{1-6}$ alkylamino group; or a halogen atom, or
$R^2$ and $R^5$ are joined to form, together with the carbon atom bonded thereto, a 3- to 8-membered carbocycle or heterocycle each optionally substituted by a substituent selected from (1) an oxo group, (2) a $C_{1-6}$ alkyl group optionally substituted by a $C_{1-6}$ alkoxy group, and (3) a phenyl group optionally substituted by a $C_{1-6}$ alkoxy-carbonyl group.
[5] The support of the above-mentioned [4], wherein $L^1$ is a succinyl group.
[6] The support of the above-mentioned [4] or [5], wherein $L^1$ and $L^2$ are succinyl groups.
[7] The support of any of the above-mentioned [4] to [6], wherein $X^1$ and $X^2$ are dimethoxytrityl groups.
[8] The support of according to any of the above-mentioned [4] to [7], wherein Sp is a solid phase support comprised of porous synthetic polymer particles or porous glass particles.
[9] A method of producing a nucleic acid, comprising a step of performing a nucleic acid synthesis reaction on the support of any of the above-mentioned [4] to [8].
[10] The production method of the above-mentioned [9], wherein the nucleic acid synthesis reaction is performed by a solid phase phosphoramidite method.

Effect of the Invention

The linker for solid phase synthesis of nucleic acid of the present invention is a universal linker, and the support for nucleic acid synthesis of the present invention, carrying the linker is a universal support. The support for nucleic acid synthesis carrying the linker of the present invention does not require a support for solid phase synthesis carrying a nucleotide to be the 3' terminal of the nucleic acid desired to be synthesized, and can synthesize a nucleic acid having a hydroxy group introduced into the 3' terminal at a high purity. It does not require a support for solid phase synthesis with a modified nucleoside or nucleotide carried in advance even when synthesizing a modified oligonucleotide, and can synthesize a nucleic acid having a hydroxy group introduced into the 3' terminal at a high purity.

Therefore, the support for nucleic acid synthesis of the present invention is preferably used for automatic synthesis of a nucleic acid having a hydroxy group at the 3' terminal. Furthermore, the production method of a nucleic acid using the support for nucleic acid synthesis of the present invention does not require separate introduction of a hydroxy group into the 3' terminal of a synthesized nucleic acid, unlike conventional methods.

DESCRIPTION OF EMBODIMENTS

The term "nucleic acid" as used herein refers to a linear compound (oligonucleotide) wherein nucleotides are connected via phosphodiester bonds, and is understood to encompass DNA, RNA and the like. The nucleic acid may be single-stranded or double-stranded. Since it allows an efficient synthesis using a nucleic acid synthesizer, the nucleic acid is preferably single-stranded. The "nucleic acid" in the present specification includes not only a oligonucleotide containing a purine base such as adenine (A), guanine (G) and the like and a pyrimidine base such as thymine (T), cytosine (C), uracil (U) and the like but also a modified oligonucleotide containing other modified heterocyclic base.

The nucleotide length of the nucleic acid is not particularly limited, and the nucleic acid is preferably 2 to 200 nucleotides long. If the nucleic acid is too long, the yield and purity of the nucleic acid obtained decrease.

The "linker" in the present specification refers to a molecule that links two substances via a covalent bond. In the present invention, the linker connects a solid phase support and a nucleic acid.

The linker for solid phase synthesis of nucleic acid of the present invention is represented by the following formula.

wherein, $X^1$ and $X^2$ are each independently a hydroxy-protecting group to be dissociated by acid.

Examples of the protecting group include a trityl group (Tr), a monomethoxytrityl group (MMTr), a dimethoxytrityl group (DMTr) and the like. These protecting groups can be dissociated using a dichloromethane or toluene solution of Bronsted acid such as trichloroacetic acid, dichloroacetic acid and the like. Since deprotection with an acid is easy, $X^1$ and $X^2$ are preferably DMTr.

$L^1$ and $L^2$ are each independently a linkage moiety to be cleaved by alkali, and at least one of $L^1$ and $L^2$ only needs to be linkable to a support for nucleic acid solid phase synthesis.

Examples of $L^1$ and $L^2$ include, but are not limited to, a succinyl group (succinyl linker), an acetyl group or Q linker (Pon et al., Nucleic Acids Res., 27, 1531 (1999)) and the like. To minimize the number of steps of linker synthesis and reduce the cost, at least one of $L^1$ and $L^2$ is preferably a succinyl group, more preferably $L^1$ and $L^2$ are succinyl groups. These linkage moieties can be easily cleaved by hydrolysis with aqueous ammonia, aqueous ammonia/methylamine mixture and the like, and oligonucleotide is cleaved from a support for solid phase synthesis after completion of automatic synthesis. That is, when molecules with synthesized oligonucleotide bound at the $X^1$ and $X^2$ positions are produced, it is considered that $L^1$ and $L^2$ are cleaved from the linker for solid phase synthesis of nucleic acid of the present invention, which is shown by the above-mentioned formula, simultaneously with which the linker of the present invention is released from the synthetic oligonucleotide due to the nucleophilic reaction of "O$^-$" produced and attacks the phosphorus atom at the 3' terminal to form a cyclic phosphate ester, whereby a synthetic oligonucleotide having a hydroxy group at the 3' terminal can be obtained. The reaction as such universal support of the present invention is described later.

$R^1$-$R^6$ are each independently a hydrogen atom; a $C_{1-6}$ alkyl group optionally substituted by a $C_{1-6}$ alkoxy group; a $C_{1-6}$ alkoxy group; a $C_{1-7}$ acyl group; a mono or di-$C_{1-6}$ alkylamino group; or a halogen atom, or $R^2$ and $R^5$ are joined to form, together with the carbon atom bonded thereto, a 3- to 8-membered carbocycle or heterocycle each optionally substituted by a substituent selected from (1) an oxo group, (2) a $C_{1-6}$ alkyl group optionally substituted by a $C_{1-6}$ alkoxy group, and (3) a phenyl group optionally substituted by a $C_{1-6}$ alkoxy-carbonyl group.

In the present specification, examples of the "$C_{1-6}$ alkyl group" include methyl group, ethyl group, n-propyl group, isopropyl group, n-butyl group, isobutyl group, sec-butyl group, tert-butyl group, n-amyl group, isoamyl group, sec-amyl group, tert-amyl group, hexyl group and the like. Of these, methyl group or ethyl group is preferable.

In the present specification, examples of the "$C_{1-6}$ alkoxy group" include methoxy group, ethoxy group, n-propoxy group, isopropoxy group, n-butoxy group, isobutoxy group, sec-butoxy group, tert-butoxy group, pentyloxy group, hexyloxy group and the like. Of these, methoxy group is preferable.

In the present specification, examples of the "$C_{1-6}$ alkyl group optionally substituted by a $C_{1-6}$ alkoxy group" include those exemplified for the above-mentioned "$C_{1-6}$ alkyl group", and methoxymethyl group, methoxyethyl group, methoxy-n-propyl group, methoxyisopropyl group, ethoxymethyl group, n-propoxymethyl group, n-butoxymethyl group and the like. Of these, methyl group, ethyl group, methoxymethyl group or methoxyethyl group is preferable.

In the present specification, as the "$C_{1-7}$ acyl group",
(1) formyl group,
(2) carboxy group,
(3) $C_{1-6}$ alkyl-carbonyl group,
(4) $C_{1-6}$ alkoxy-carbonyl group,
and the like can be mentioned.

Examples of the "$C_{1-6}$ alkyl-carbonyl group" include acetyl group, propanoyl group, butanoyl group, isobutanoyl group, pentanoyl group, isopentanoyl group, hexanoyl group and the like. Of these, acetyl group is preferable.

Examples of the "$C_{1-6}$ alkoxy-carbonyl group" include methoxycarbonyl group, ethoxycarbonyl group, n-propoxycarbonyl group, isopropoxycarbonyl group, n-butoxycarbonyl group, pentyloxycarbonyl group, hexyloxycarbonyl group and the like. Of these, methoxycarbonyl group is preferable.

Of the above-mentioned "$C_{1-7}$ acyl group", $C_{1-6}$ alkoxy-carbonyl group is preferable, and methoxycarbonyl group is particularly preferable.

In the present specification, examples of the "mono or alkylamino group" include methylamino group, ethylamino group, n-propylamino group, isopropylamino group, n-butylamino group, isobutylamino group, sec-butylamino group, tert-butylamino group, n-amylamino group, isoamylamino group, sec-amylamino group, tert-amylamino group, hexylamino group, dimethylamino group, diethylamino group, di-n-propylamino group, diisopropylamino group, di-n-butylamino group and the like. Of these, methylamino group, dimethylamino group, ethylamino group or diethylamino group is preferable.

In the present specification, examples of the "halogen atom" include chlorine atom, fluorine atom, bromine atom and iodine atom. Of these, chlorine atom or fluorine atom is preferable.

In the present specification, examples of the "3- to 8-membered carbocycle" include $C_{3-8}$ cycloalkane such as cyclopropane, cyclobutane, cyclopentane, cyclohexane, cycloheptane, cyclooctane and the like; and $C_{3-8}$ cycloalkene such as cyclopropene, cyclobutene, cyclopentene, cyclohexene, cycloheptene, cyclooctene and the like. Of these, $C_{5-6}$ cycloalkane or $C_{5-6}$ cycloalkene is preferable.

In the present specification, examples of the "3- to 8-membered heterocycle" include 3- to 8-membered (preferably 5- or 6-membered) aromatic heterocyclic group and nonaromatic heterocyclic group containing, as a ring-constituting atom besides carbon atom, 1 to 4 hetero atoms selected from an oxygen atom, a sulfur atom and a nitrogen atom, for example, 3- to 8-membered aromatic heterocycle such as furan, thiophene, pyridine, pyrimidine, pyridazine, pyrazine, pyrrole, imidazole, pyrazole, thiazole, isothiazole, oxazole, isoxazole, oxadiazole, thiadiazole, triazole, triazine and the like; 3- to 8-membered non-aromatic heterocycle such as aziridine, azetidine, pyrrolidine, piperidine, morpholine, thiomorpholine, piperazine, hexamethylenimine, oxazolidine, thiazolidine, imidazolidine, oxazoline, thiazoline, imidazoline, dioxole, dioxolane, dihydrooxadiazole, pyran, dihydropyran, tetrahydropyran, thiopyran, tetrahydrothiopyran, dihydrofuran, tetrahydrofuran, pyrazolidine, pyrazoline, dihydropyridine, tetrahydropyridine, dihydropyrimidine, tetrahydropyrimidine, dihydrotriazole, tetrahydrotriazole and the like; and the like. Of these, 5- or 6-membered non-aromatic heterocycle (preferably tetrahydrofuran, pyrrolidine) is preferable.

In the present specification, examples of the "phenyl group optionally substituted by a $C_{1-6}$ alkoxy-carbonyl group" include phenyl group, 2-methoxycarbonylphenyl group, 3-methoxycarbonylphenyl group, 4-methoxycarbonylphenyl group, 2-ethoxycarbonylphenyl group, 3-ethoxycarbonylphenyl group, 4-ethoxycarbonylphenyl group, 2-n-propoxycarbonylphenyl group, 3-n-propoxycarbonylphenyl group, 4-n-propoxycarbonylphenyl group, 2-isopropoxycarbonylphenyl group, 3-isopropoxycarbonylphenyl group, 4-isopropoxycarbonylphenyl group and the like. Of these, phenyl group, 2-methoxycarbonylphenyl group, 3-methoxycarbonylphenyl group, 4-methoxycarbonylphenyl group, 2-ethoxycarbonylphenyl group, 3-ethoxycarbonylphenyl group, 4-ethoxycarbonylphenyl group, 2-ethoxycarbonylphenyl group, 3-ethoxycarbonylphenyl group or 4-ethoxycarbonylphenyl group is preferable.

$R^1$ is preferably a hydrogen atom.
$R^3$ is preferably a hydrogen atom.
$R^4$ is preferably a hydrogen atom.
$R^6$ is preferably a hydrogen atom.
$R^2$ is preferably a $C_{1-7}$ acyl group, more preferably a $C_{1-6}$ alkoxy-carbonyl group, particularly preferably a methoxycarbonyl group.
$R^5$ is preferably a $C_{1-7}$ acyl group, more preferably a $C_{1-6}$ alkoxy-carbonyl group, particularly preferably a methoxycarbonyl group.

Alternatively, $R^2$ and $R^5$ are joined to form, together with the carbon atom bonded thereto, a 5- or 6-membered non-aromatic heterocycle (preferably tetrahydrofuran or pyrrolidine) each optionally substituted by a substituent selected from (1) an oxo group, (2) a $C_{1-6}$ alkyl group substituted by a $C_{1-6}$ alkoxy group, and (3) a phenyl group substituted by a $C_{1-6}$ alkoxy-carbonyl group.

The solid phase support for solid phase synthesis of nucleic acid of the present invention carries the above-mentioned linker for solid phase synthesis of nucleic acid of the present invention, and is represented by the following formula wherein $X^1$ and $X^2$, $L^1$ and $L^2$, and $R^1$-$R^6$ are as defined above.

Sp is a solid phase support. For convenience, Sp is bound to $L^1$, but may be bound to $L^2$. The solid phase support is not particularly limited as long as a reagent used in excess can be easily removed by washing and, for example, glass porous support, porous synthetic polymer support such as polystyrene support, acrylamide support etc., and the like can be mentioned.

In a preferable embodiment of the present invention, in the above-mentioned formula, Sp is a glass porous support.

Here, the "glass porous support" refers to a porous support containing glass as a constituent component and examples thereof include, but are not limited to, porous glass particles in a granular shape (CPG) and the like. More specifically, as the aforementioned CPG, a CPG solid phase support having a long chain aminoalkyl spacer (LCAA-CPG solid phase support) is preferably used, and further, for the synthesis of a long chain nucleotide, one having a CPG pore of preferably 20-400 nm, more preferably 50-200 nm, most preferably 100 nm, is used.

In another preferable embodiment of the present invention, in the above-mentioned formula, Sp is a polystyrene support. Here, the "polystyrene support" is a solid phase support constituted with a copolymer containing structural unit (A) represented by the following formula:

and/or a substituted derivative thereof as a structural unit. Examples of the substituted derivatives of the structural unit (A) include a compound wherein one or more hydrogen atoms contained in the structural unit (A) (including hydrogen atom of benzene ring) are substituted by an alkyl group having a carbon number of 1-6 (e.g., methyl group, ethyl group, n-propyl group, isopropyl group, n-butyl group, isobutyl group, sec-butyl group, tert-butyl group, n-amyl group, isoamyl group, sec-amyl group, tert-amyl group), a halogen atom, an amino group, a hydroxy group, a carboxyl group, a sulfone group, a cyano group, a methoxy group, a nitro group, a vinyl group and the like. The substituent is preferably an amino group or a hydroxy group. The position of the substituent is not particularly limited, and is preferably the para-position with respect to the main chain on the benzene ring. A preferable substitution derivative of the structural unit (A) is the hydroxystyrene structural unit (B) shown in the following formula.

The amount of structural unit (A) and/or substitution derivatives thereof relative to the total amount of the structural units contained in the copolymer constituting the polystyrene support is not particularly limited, and is generally 50 to 100% by weight, preferably 60 to 100% by weight.

Specific examples of the monomer compound copolymerizable with the above-mentioned structural unit (A) include, but are not limited to, styrene; nucleus alkyl substituted styrene such as o-methylstyrene, m-methylstyrene, p-methylstyrene, 2,4-dimethylstyrene, ethylstyrene, trimethylstyrene, and p-t-butylstyrene and the like; α-alkyl substituted styrene such as α-methylstyrene, α-methyl-p-methylstyrene and the like; nucleus halogenated styrene such as chlorostyrene, dichlorostyrene, fluorostyrene, pentafluorostyrene, bromostyrene and the like; alkyl halide styrene such as chloromethylstyrene, fluoromethylstyrene and the like; hydroxystyrene; hydroxymethylstyrene; vinyl benzoate; sodium styrenesulfonate; cyanostyrene; methoxystyrene; ethoxystyrene; butoxy styrene; nitrostyrene; acyloxy styrene such as acetoxystyrene, benzoxystyrene etc., and the like. Further examples include, but are not limited to, alkyl(meth)acrylate monomer such as methyl(meth)acrylate, ethyl(meth)acrylate, propyl(meth)acrylate, butyl(meth)acrylate and the like, vinyl cyanide monomer such as acrylonitrile, methacrylonitrile, ethacrylonitrile etc., and the like.

In another embodiment of the present invention, in the above-mentioned formula, Sp may be a solid phase support consisting of styrene-hydroxystyrene-divinylbenzene copolymer particles (JP-A-2005-097545, JP-A-2005-325272 and J-PA-2006-342245) or a styrene-(meth)acrylonitrile-hydroxystyrene-divinylbenzene copolymer (JP-A-2008-074979), having, in addition to the above-mentioned structural units (A) and (B), divinylbenzene structural unit (C) represented by the following formula:

and the like. In addition, one or more hydrogen atoms (including hydrogen atom of benzene ring) in the above-mentioned divinylbenzene structural unit (C) may be substituted by an alkyl group having a carbon number of 1-6 (e.g., methyl group, ethyl group, n-propyl group, isopropyl group, n-butyl group, isobutyl group, sec-butyl group, tert-butyl group, n-amyl group, isoamyl group, sec-amyl group, tert-amyl group), a halogen atom, an amino group, a hydroxy group, a carboxyl group, a sulfone group, a cyano group, a methoxy group, a nitro group, a vinyl group and the like. The substituent is preferably an amino group or a hydroxy group.

In the above-mentioned formula, when Sp is a solid phase support comprised of the aforementioned styrene-(meth)acrylonitrile-hydroxystyrene-divinylbenzene copolymer, the structural unit of (meth)acrylonitrile may contain each or both of the structural units of acrylonitrile and methacrylonitrile. When the amount of the structural unit of (meth)acrylonitrile to the total amount of the structural unit of the styrene-(meth)acrylonitrile-hydroxystyrene-divinylbenzene copolymer is too high or too low, the degree of swelling greatly varies depending on the kind of organic solvent. Therefore, the amount is preferably 2-11 mmol/g.

In another preferable embodiment of the present invention, in the above-mentioned formula, Sp is an acrylamide support. More specifically, in the above-mentioned formula, Sp may be a support for solid phase synthesis, which is comprised of, in addition to the above-mentioned structural units (A) and (C), an aromatic monovinyl compound-divinyl compound-(meth)acrylamide derivative copolymer further containing a (meth)acrylamide derivative monomer.

In the above-mentioned formula, when Sp is a solid phase support comprised of the aforementioned aromatic monovinyl compound-divinyl compound-(meth)acrylamide derivative copolymer, the aforementioned aromatic monovinyl compound is not particularly limited. For example, styrene; nucleus alkyl substituted styrene such as o-methylstyrene, m-methylstyrene, p-methylstyrene, 2,4-dimethylstyrene, ethylstyrene, trimethylstyrene, p-t-butylstyrene and the like; α-alkyl substituted styrene such as α-methylstyrene, α-methyl-p-methylstyrene and the like; nucleus halogenated styrene such as chlorostyrene, dichlorostyrene, fluorostyrene, pentafluorostyrene, bromostyrene and the like; alkyl halide styrene such as chloromethylstyrene, fluoromethylstyrene and the like; hydroxystyrene; hydroxymethylstyrene; vinyl benzoate; sodium styrenesulfonate; cyanostyrene; methoxystyrene; ethoxystyrene; butoxy styrene; nitrostyrene; acyloxystyrene such as acetoxystyrene, benzoxystyrene etc., and the like can be mentioned, with preference given to styrene.

Examples of the aforementioned (meth)acrylamide derivative include, but are not limited to, N-alkyl(meth)acrylamide; N,N-dialkyl(meth)acrylamide; N-alkoxyalkyl(meth)acrylamide; 2-(meth)acrylamide alkane sulfonic acid; N-alkylol (meth)acrylamide such as N-methylol(meth)acrylamide and the like; acrylamide; methacrylamide; diacetone acrylamide; N,N-dimethyl aminopropylacrylamide; acryloylmorpholine; N-phenoxymethyl(meth)acrylamide and the like.

In addition, the alkyl contained in the aforementioned N-alkyl(meth)acrylamide is generally a linear or branched alkyl having a carbon number of 1-6, preferably 1-3. Examples of the N-alkyl(meth)acrylamide include N-methyl(meth)acrylamide, N-ethyl(meth)acrylamide, N-n-propyl(meth)acrylamide, N-isopropyl(meth)acrylamide, N-tert-butyl(meth)acrylamide, and N-lauryl(meth)acrylamide and the like.

The two alkyls contained in the aforementioned N,N-dialkyl(meth)acrylamide are each generally a linear or branched alkyl having a carbon number 1-6, preferably 1-3. Examples of the N,N-dialkyl(meth)acrylamide include N,N-dimethyl(meth)acrylamide, N,N-diethyl(meth)acrylamide, N,N-diisopropyl(meth)acrylamide, N,N-di-tert-butyl(meth)acrylamide, N,N-dilauryl(meth)acrylamide, N,N-di-tert-octyl(meth)acrylamide, N,N-dilauryl(meth)acrylamide, N,N-dicyclohexyl(meth)acrylamide and the like.

The alkoxy contained in the aforementioned N-alkoxyalkyl(meth)acrylamide is generally a linear or branched alkoxy having a carbon number of 1-6, preferably 1-3. The alkyl contained in N-alkoxyalkyl(meth)acrylamide is generally a linear or branched alkyl having a carbon number of 1-6, preferably 1-3. Examples of the N-alkoxyalkyl(meth)acrylamide include N-methoxymethyl(meth)acrylamide, N-ethoxymethyl(meth)acrylamide, N-propoxymethyl(meth)acrylamide, N-butoxy methyl(meth)acrylamide, N-ethoxyethyl(meth)acrylamide, N-methoxypropyl(meth)acrylamide, N-ethoxypropyl(meth)acrylamide, N-isopropoxyethyl(meth)acrylamide and the like.

The alkane contained in the aforementioned 2-(meth)acrylamide alkanesulfonic acid is generally a linear or branched alkane having a carbon number of 1-6, preferably 1-3. Examples of the 2-(meth)acrylamide alkanesulfonic acid include 2-acrylamide propanesulfonic acid, 2-acrylamide-n-butanesulfonic acid, 2-acrylamide-n-hexanesulfonic acid, 2-acrylamide-2-methylpropanesulfonic acid and the like.

The aforementioned (meth)acrylamide derivative is preferably diacetone acrylamide, N-isopropyl(meth)acrylamide, N-methoxymethyl(meth)acrylamide or N,N-dimethyl(meth)acrylamide.

A typical structural unit derived from (meth)acrylamide derivative monomer includes the following structural units.

In the above-mentioned formula, when Sp is an acrylamide solid phase support and the content of the structural unit derived from a (meth)acrylamide derivative monomer is too small, an effect of avoiding a decrease in the synthesis amount of nucleic acid and a decrease in the synthesis purity cannot be obtained. On the other hand, when it is too high, a porous resin bead is difficult to form. Therefore, it is preferably 0.3-4 mmol/g, more preferably 0.4-3.5 mmol/g, further preferably 0.6-3 mmol/g.

The porous particle to be used as the support for solid phase synthesis of the present invention is preferably one having a functional group that contributes to nucleic acid synthesis. The "contributes to nucleic acid synthesis" refers to a functional group which can be the starting point of nucleic acid synthesis and to which a linker can be added. Specifically, an amino group, a hydroxy group and the like can be mentioned.

The content of the functional group that contributes to nucleic acid synthesis is not particularly limited. When the content of the functional group is too small, the yield of nucleic acid decreases and when it is too high, the purity of the obtained nucleic acid decreases. Therefore, it is preferably 10-2000 µmol/g, more preferably 50-1000 µmol/g, further preferably 100-800 µmol/g.

When the functional group that contributes to nucleic acid synthesis is a hydroxy group, the amount of the hydroxy group of the porous particles of the present invention is measured by titration based on JIS K0070. Specifically, an acetylation reagent is produced by adding pyridine to 25 g of acetic anhydride to the total amount of 100 mL. The above-mentioned acetylation reagent (0.5 mL), pyridine (4.5 mL) and a sample (about 0.5 g) are placed in a flask, and the mixture is heated at 95-100° C. for 2 hr to acetylate the hydroxy group. Then, distilled water (1 mL) is added into the flask, and the mixture is heated to decompose acetic anhydride that was not consumed by acetylation to acetic acid. The amount of the acetic acid is measured by neutralization titration using 0.5 mol/L of aqueous potassium hydroxide solution. Separately, a blank measurement is performed in the same way, but without adding the sample. Since the difference in the number of moles in the above-mentioned two measurements is the number of moles of acetic anhydride consumed by acetylation of the hydroxy group of the sample (i.e., amount of hydroxy group of the sample), this value is divided by the sample weight to determine the amount of the hydroxy group per 1 g of the sample.

The amount of the linker to be bound to the solid phase support is not particularly limited. When the linker content is too low, the yield of nucleic acid decreases. When the linker content is too high, the purity of the nucleic acid obtained tends to decrease and the number of nucleotides of the obtained nucleic acid tends to decrease. Therefore, it is preferably within the range of 20-800 µmol/g, more preferably 25-500 µmol/g.

The shape of the aforementioned porous solid phase support is not particularly limited and may be any shape of plate, particle, fiber and the like. Since the packing efficiency to a synthesis reaction container can be enhanced, and the reaction container is not easily broken, a porous synthetic polymer having a particle shape is preferable.

The term "particle" in the specification does not mean being exactly spherical, but means having any constant form (e.g., roughly spherical forms such as ellipse spherical, polygonal form, cylindrical form, irregular forms such as konpeito form, and the like).

While the size (volume) of one particle of the porous synthetic polymer particles is not particularly limited, when the average particle size measured by laser diffraction (scattering type) of the porous particles is smaller than 1 µm, inconvenience occurs when it is packed in a column and used in that the back pressure becomes too high or a solution sending rate becomes slow. On the other hand, when the average particle size is more than 1000 µm, the gap between the support particles becomes large and efficient packing of support particles in a column having a predetermined volume becomes difficult. Therefore, it is preferably 1-1000 µm, more preferably 5-500 µm, further preferably 10-200 µm.

While the specific surface area of the aforementioned synthetic polymer particles measured by a multi-point BET method is not particularly limited, when the specific surface area is less than 0.1 m$^2$/g, the degree of swelling in an organic solvent becomes low, and a synthesis reaction tends to be difficult to occur. On the other hand, when it is more than 500 m$^2$/g, fine pore size becomes small, and a synthesis reaction tends to be difficult to occur. Therefore, the specific surface area is preferably 0.1-500 m$^2$/g, more preferably 10-300 m$^2$/g, further preferably 50-200 m$^2$/g.

In addition, the average fine pore size of the aforementioned synthetic polymer particles measured by a mercury intrusion technique is not particularly limited. However, when the pore size is too small, the field of the synthesis reaction becomes small and a desired reaction does not occur easily, or the nucleotide length tends to be less than a desired number. On the other hand, when the pore size is too large, the frequency of contact between a hydroxy group and a substance involved in the reaction on the surface of polymer particles, which is the reaction field, decreases to lower the yield. Therefore the average fine pore size is preferably 1-200 nm, more preferably 5-100 nm, more preferably 20-70 nm.

In a preferable embodiment of the solid phase support of the present invention, in the above-mentioned formula, Sp is a low swelling cross-linking polystyrene particle commercially available as NittoPhase (registered trade mark) (manufactured by NITTO DENKO Co., Ltd.). A solid phase nucleic acid synthesis method using NittoPhase (registered trade mark) is preferably used since it shows a small peak area due to impurity and guarantees high yield and high purity in a wide scale from labo scale to mass synthesis system.

Production Method of Support for Solid Phase Synthesis of Nucleic Acid of the Present Invention While the production method of the support for solid phase synthesis of nucleic acid of the present invention is not particularly limited, for example, the support can be produced by the following method.

Alkyne (e.g., acetylene, dimethylacetylene) is reacted with furan and the like to synthesize a diepoxynaphthalene derivative. Then, using osmium tetroxide as a catalyst, the derivative is oxidized, and reacted with 4,4'-dimethoxytritylchloride and the like to protect a part of the hydroxy groups with a dimethoxytrityl group (DMTr group). Thereafter, this compound is reacted with succinic anhydride together with dichloromethane and triethylamine to bind a succinyl linker moiety to the remaining hydroxy group, which is then bound with a solid phase support having —OH group or —NH$_2$ group to give the support for solid phase synthesis of nucleic acid of the present invention.

Synthesis Method of Nucleic Acid Using Support for Solid Phase Synthesis of Nucleic Acid of the Present Invention For nucleic acid synthesis using the support for solid phase synthesis of nucleic acid of the present invention, a nucleic acid automatic synthesizer is used and various synthesis methods known per se can be used. In the present specification, the "nucleic acid synthesis reaction" particularly means an elongation reaction of nucleotide constituting a nucleic acid. Hence, nucleotides are sequentially bound to a nucleoside, nucleotide or oligonucleotide bound to the solid phase support, whereby an elongated oligonucleotide is obtained.

The nucleic acid synthesis reaction can be performed by the H-phosphonate method, phosphoester method, solid phase phosphoramidite method and the like. Of these, since high capacity of synthesizing nucleic acid and high purity of nucleic acid obtained, a solid phase phosphoramidite method is preferable.

A preferable embodiment of the nucleic acid synthesis reaction by a solid phase phosphoramidite method includes, for example, a method consisting of each of the following steps:

(a) a step of placing the support for solid phase synthesis of nucleic acid of the present invention in a reaction column of a nucleic acid automatic synthesizer;

(b) a step of flowing an acid such as dichloroacetic acid solution and the like in the reaction column to remove the hydroxymethyl-protecting group and wash the support;

(c) a step of sequentially performing respective steps of coupling to bind nucleoside phosphoramidite corresponding to the 3' terminal, which is activated by tetrazole and the like, to the aforementioned hydroxymethyl group, capping of unreacted hydroxy group, and oxidation of phosphite, and repeating the series of steps until the object sequence is obtained; and

(d) a step of immersing the support for solid phase synthesis of nucleic acid to cleave the linkage moiety after completion of the synthesis step by the apparatus, thereby affording the object nucleic acid.

As a result of the aforementioned production method, a chemical reaction shown by the following formula occurs, and a nucleic acid having a hydroxy group at the 3' terminal is produced. To be specific, in the nucleic acid synthesis method using support (A) for solid phase synthesis of nucleic acid, which is shown in Example 2 as a preferable embodiment of the present invention, the chemical reaction shown by the following formula occurs, and a nucleic acid having a hydroxy group at the 3' terminal is produced.

wherein sphere shows a solid phase support, Ac shows an acetyl group and Nuc shows a nucleic acid.

In addition, in the nucleic acid synthesis method using supports (B) and (C) for solid phase synthesis of nucleic acid of the present invention, which is shown in Examples 4 and 6 as a preferable embodiment of the present invention, a chemi-cal reaction shown by the following formula occurs, and a nucleic acid having a hydroxy group at the 3' terminal is produced.

wherein sphere shows a solid phase support and Nuc shows a nucleic acid.

Examples of the activating agent to be used in the nucleic acid production method of the present invention include, but are not limited to, 1H-tetrazole, 4,5-dicyanoimidazole, 5-ethylthio-1H-tetrazole, benzimidazolium triflate (BIT), N-phenylbenzimidazoliumtriflate, imidazoliumtriflate (IMT), N-PhIMP, 5-nitrobenzimidazoliumtriflate, triazoliumtriflate, 1-hydroxybenzotriazole (HOBT), N-(cyanomethyl)pyrrolidinium tetrafluoroborate and the like.

EXAMPLES

The present invention is explained in more detail in the following by referring to Examples, which are not to be construed as limitative.

Example 1

Preparation of Support (A) for Nucleic Acid Solid Phase Synthesis

Dimethyl acetylenedicarboxylate and furan were added to a Schlenk flask, and the mixture was reacted at room temperature for 29 days. The yield of this reaction was 22%. Using osmium tetroxide as a catalyst, the resultant product was oxidized. Then, the product was reacted with 4,4'-dimethoxytritylchloride and the like, a part of the hydroxy groups was protected with a DMTr group. Thereafter, a porous polystyrene solid phase support having a hydroxy group (manufactured by NITTO DENKO Co., Ltd., NittoPhase (registered trade mark)), which had been introduced with a succinyl group, was dispersed in acetonitrile, the aforementioned compound, HBTU and N,N-diisopropylethylamine were added, and the mixture was reacted at 28° C. for 23 hr to carry the aforementioned compound on the solid phase support. Successively, 4-dimethylaminopyridine, acetonitrile, ethanol, diisopropylethylamine and HBTU were added, and the mixture was reacted at 28° C. for 20 hr to cap the unreacted carboxy groups. Acetic anhydride, N-methylimidazole, pyridine, 4-dimethylaminopyridine and acetonitrile were added, and the mixture was reacted at 28° C. for 22 hr to cap the hydroxy groups, whereby solid phase support (A) for nucleic acid synthesis of the present invention was obtained, which is represented by the following formula:

wherein the sphere shows a solid phase support, and Ac shows an acetyl group.

The binding amount of the linker of the present invention to the solid phase support obtained as mentioned above was 41 μmol/g.

Example 2

Synthesis of 20-Mer DNA Using Support (A) for Solid Phase Synthesis of Nucleic Acid The solid phase support (A) for nucleic acid synthesis of the present invention (24.3 mg) prepared in Example 1 was packed in a reaction column, and a 20 mer DNA oligonucleotide (5'-ATACCGATTAAGCGAAGTTT-3': SEQ ID NO: 1) was synthesized by DMT-on (method without removing 5'-terminal protecting group) (synthesis scale 1 μmol) using an automated DNA/RNA synthesizer ABI3400 (manufactured by Applied Biosystems). After the synthesis, the solid phase support, with which the DNA oligonucleotide was bound, was immersed in a 30% aqueous ammonia/ethanol (3:1) mixed solution at 55° C. for 15 hr to cleave the DNA oligonucleotide from the solid phase support.

Comparative Example 1

Synthesis of 20-Mer DNA Using Support for Solid Phase Synthesis Bound with DMT-dT-3'-Succinate In the same manner as in Example 1, cleavable linker DMT-dT-3'-succinate (manufactured by Beijing OM Chemicals) was bound with a commercially available solid phase support NittoPhase (registered trade mark) (manufactured by NITTO DENKO Co., Ltd.). The binding amount of the compound to the solid phase support was 42 μmol/g. This solid phase support (23.8 mg) was filled in a reaction column, and a 20 mer DNA oligonucleotide (5'-ATACCGATTAAGC-GAAGTTT-3': SEQ ID NO: 1) was synthesized by DMT-on (method without removing 5'-terminal protecting group) (synthesis scale 1 μmol) in the same manner as in Example 2. After synthesis, the DNA oligonucleotide was cleaved from the solid phase support.

Experimental Example 1

Figure 1:
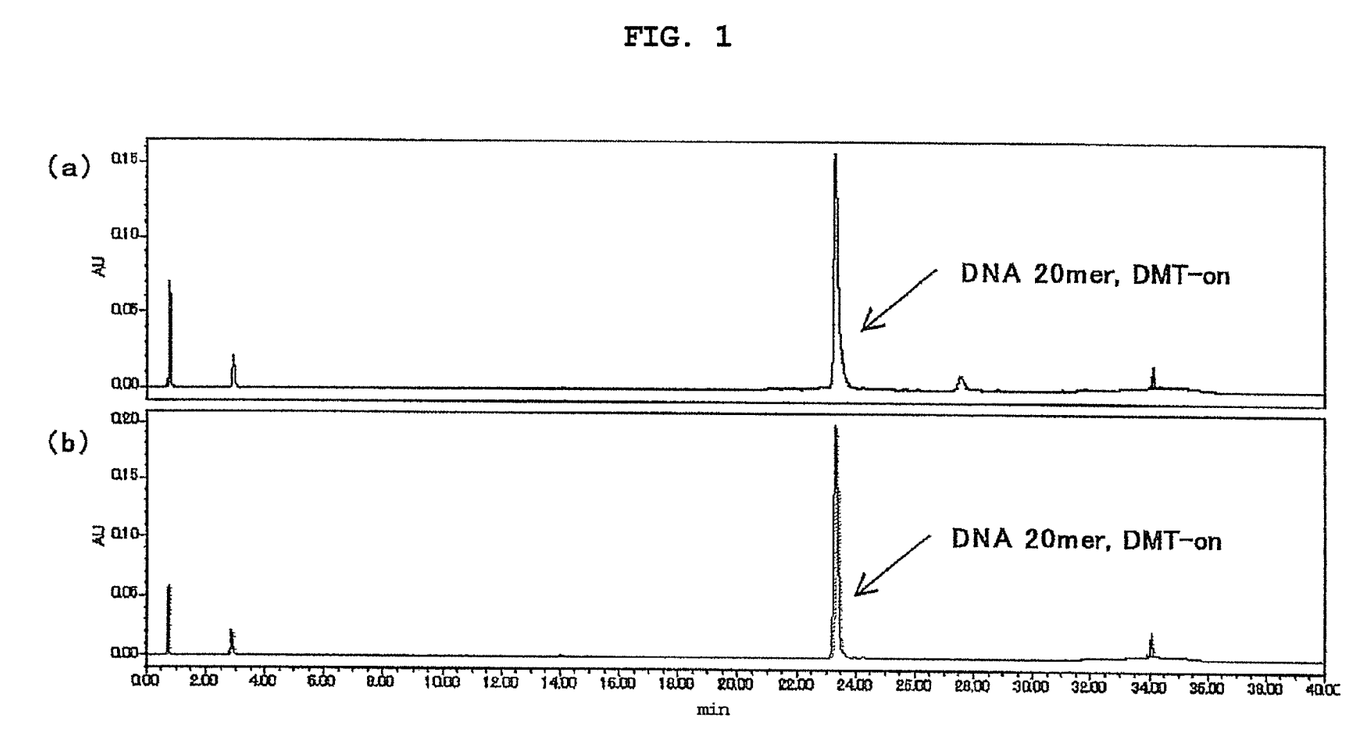
FIG. 1 shows HPLC chart of the DNA oligonucleotide solutions obtained in Example 2 (a) and Comparative Example 1 (b).

The DNA oligonucleotide solutions obtained in Example 2 and Comparative Example 1 were measured by high performance liquid chromatography (HPLC) (measurement condition: column; Waters XBridge OST C18 2.5 μm 50×4.6 mm, UV detection; 260 nm, Buffer A; 100 mM HFIP/7 mM TEA in Water, pH 8.0, Buffer B; methanol, temperature; 30° C.). FIGS. 1(a) and (b) show each HPLC chart.

In addition, the DNA oligonucleotide solutions obtained in Example 2 and Comparative Example 1 were subjected to LC-MS analysis. (measurement condition: column; Waters XBridge OST C18 2.5 μm 50×4.6 mm, UV detection; 254 nm, Buffer A; HFIP/7 mM TEA in Water, pH 8.0, Buffer B; methanol, temperature; 30° C.)

As a result, the main peak of the DNA oligonucleotide produced in Example 2 was confirmed to be 20-mer DNA oligonucleotide having a hydroxy group at the 3' terminal (molecular weight (found); 6439). On the other hand, the main peak of the DNA oligonucleotide produced in Comparative Example 1 was also confirmed to be a 20-mer DNA oligonucleotide having a hydroxy group at the 3' terminal (molecular weight (found); 6439).

Example 3

Preparation of Support (B) for Nucleic Acid Solid Phase Synthesis

Dimethyl acetylenedicarboxylate and furan were added to a Schlenk flask, and the mixture was reacted at room temperature for 29 days. The yield of this reaction was 22%. Using osmium tetroxide as a catalyst, the resultant product was oxidized. Then, the product was reacted with 4,4'-dimethoxytritylchloride and the like, and a part of the hydroxy groups was protected with a DMTr group. Then, succinic anhydride and the like were added to introduce a succinyl group into the aforementioned compound. NittoPhase (registered trade mark) (manufactured by NITTO DENKO Co., Ltd.), which is a cross-linking polystyrene solid phase support having a hydroxy group was dispersed in acetonitrile, the aforementioned compound, HBTU and N,N-diisopropylethylamine were added and the mixture was reacted at 28° C. for 23 hr to carry them on the solid phase support. Thereafter, 4-dimethylaminopyridine, acetonitrile, ethanol, diisopropylethylamine and HBTU were added and the mixture was reacted at 28° C. for 20 hr to cap the unreacted carboxy group. Acetic anhydride, N-methylimidazole, pyridine, 4-dimethylaminopyridine and acetonitrile were added and the mixture was reacted at 28° C. for 22 hr to cap the unreacted hydroxy group, whereby solid phase support (B) for nucleic acid synthesis of the present invention was obtained, which is represented by the following formula:

wherein sphere shows a solid phase support.

The binding amount of the linker of the present invention to the solid phase support obtained as mentioned above was 141 μmol/g.

Example 4

Synthesis of 20-Mer DNA Using Support (B) for Nucleic Acid Solid Phase Synthesis The solid phase support (B) for nucleic acid synthesis of the present invention (7.1 mg) prepared in Example 3 was packed in a reaction column, 20-mer DNA oligonucleotide (5'-ATA CCG ATT AAG CGA AGT TT-3': SEQ ID NO: 1) was synthesized by DMT-on (method without removing 5'-terminal protecting group) (synthesis scale 1 μmol) using an automated DNA/RNA synthesizer ABI3400 (manufactured by Applied Biosystems). After the synthesis, the solid phase support, with which the DNA oligonucleotide was bound, was immersed in a 30% aqueous ammonia/ethanol (3:1) mixed solution at 55° C. for 15 hr to cleave the DNA oligonucleotide from the solid phase support.

Comparative Example 2

Synthesis of 20-Mer DNA Using Support for Solid Phase Synthesis Bound with DMT-dT-3'-Succinate In the same manner as in Comparative Example 1, a solid phase support NittoPhase, wherein 96 μmol/g of DMT-dT-3'- succinate was bound, was prepared. This solid phase support (10.4 mg) was packed in a reaction column and, in the same manner as in Example 4, 20-mer DNA oligonucleotide (5'-ATA CCG ATT AAG CGA AGT TT-3': SEQ ID NO: 1) was synthesized by DMT-on (synthesis scale 1 μmol). After the synthesis, the DNA oligonucleotide was cleaved from the solid phase support.

Experimental Example 2

Figure 2:
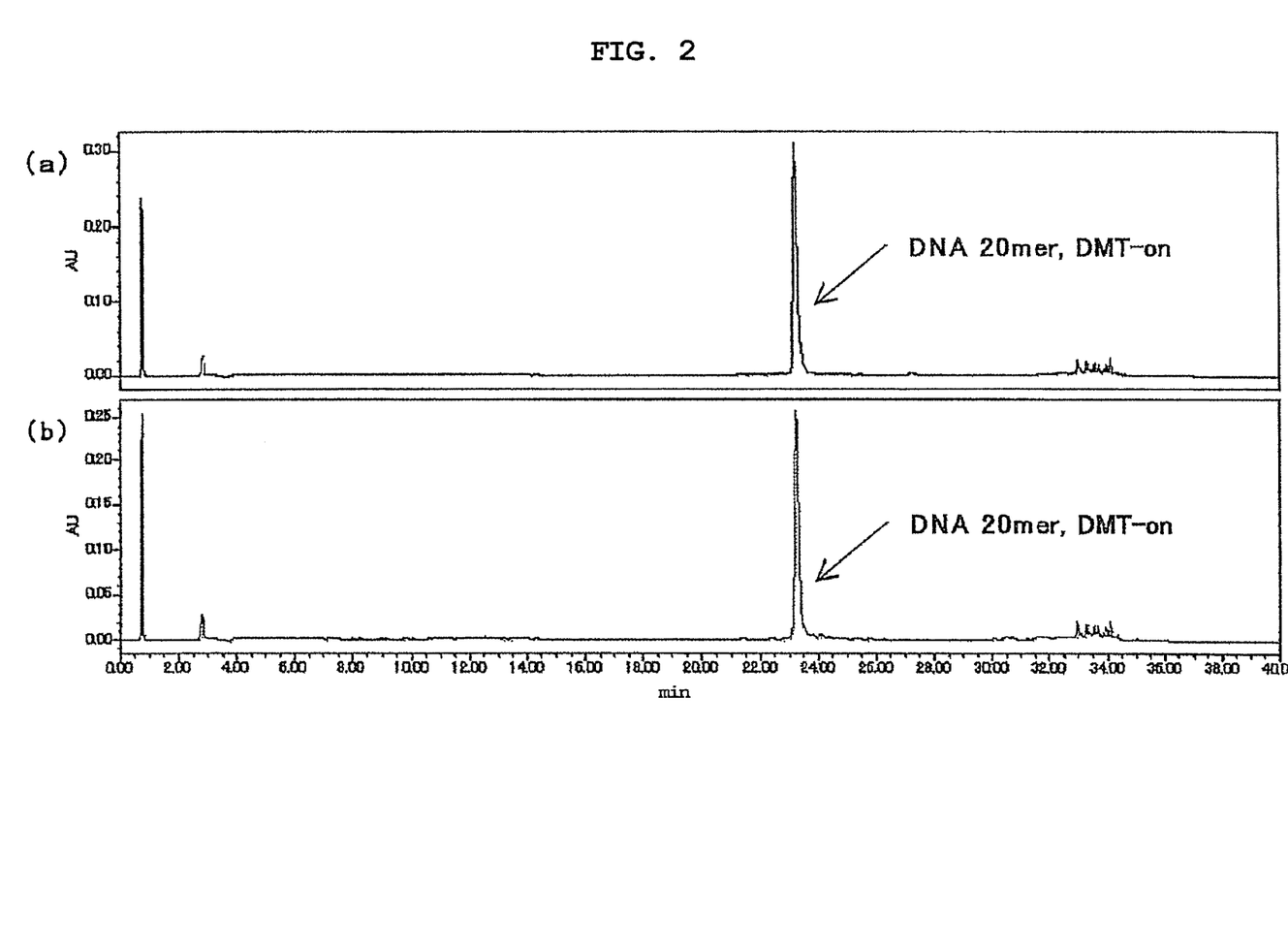
FIG. 2 shows HPLC chart of the DNA oligonucleotide solutions obtained in Example 4 (a) and Comparative Example 2 (b).

The DNA oligonucleotide solutions obtained in Example 4 and Comparative Example 2 were measured by HPLC. The measurement conditions were column; XBridge OST C18 2.5 μm 50×4.6 mm (manufactured by Waters), UV detection; 260 nm, Buffer A; 100 mM HFIP/7 mM TEA/water (pH 8.0), Buffer B; methanol, temperature: 30° C. FIGS. 2(a) and (b) show each HPLC chart.

As a result, the main peak of the DNA oligonucleotide produced in Example 4 was confirmed to be a 20-mer DNA oligonucleotide having a hydroxy group at the 3' terminal, since the detection time was the same as in Example 2. On the other hand, the main peak of the DNA oligonucleotide produced in Comparative Example 2 was also confirmed to be a 20-mer DNA oligonucleotide having a hydroxy group at the 3' terminal, since the detection time was the same as in Comparative Example 1.

Example 5

Preparation of Support (C) for Nucleic Acid Solid Phase Synthesis

Acetylenedicarboxylic acid, tetrahydrofuran and furan were added to a Schlenk flask, and the mixture was reacted at room temperature for 18 days. The yield of this reaction was 67%. The resulting dicarboxylic acid was converted to the corresponding dimethylester by a mixture of dimethyl sulfate, potassium carbonate and acetone under reflux. Using osmium tetroxide as a catalyst, the resultant product was oxidized. Then, the product was reacted with 4,4'-dimethoxytritylchloride and the like, a part of the hydroxy groups was protected with a DMTr group and the product was purified by column chromatography.

Then, succinic anhydride and the like were added to introduce a succinyl group into the aforementioned compound. NittoPhase (registered trade mark) (manufactured by NITTO DENKO Co., Ltd.), which is a cross-linking polystyrene solid phase support having a hydroxy group was dispersed in acetonitrile, the aforementioned compound, HBTU and N,N-diisopropylethylamine were added and the mixture was reacted at 28° C. for 23 hr to carry them on the solid phase support. Thereafter, 4-dimethylaminopyridine, acetonitrile, ethanol, diisopropylethylamine and HBTU were added and the mixture was reacted at 28° C. for 20 hr to cap the unreacted carboxy group. Acetic anhydride, N-methylimidazole, pyridine, 4-dimethylaminopyridine and acetonitrile were added and the mixture was reacted at 28° C. for 22 hr to cap the unreacted hydroxy group, whereby solid phase support (C) for nucleic acid synthesis of the present invention was obtained, which is represented by the following formula:

wherein sphere shows a solid phase support.

The binding amount of the linker of the present invention to the solid phase support obtained as mentioned above was 62 μmol/g.

Example 6

Synthesis of 20-Mer DNA Using Support (C) for Nucleic Acid Solid Phase Synthesis The solid phase support (C) for nucleic acid synthesis of the present invention (16.1 mg) prepared in Example 5 was packed in a reaction column, 20-mer DNA oligonucleotide (5'-ATA CCG ATT AAG CGA AGT TT-3': SEQ ID NO: 1) was synthesized by DMT-on (method without removing 5'-terminal protecting group) (synthesis scale 1 μmol) using an automated DNA/RNA synthesizer AB13400 (manufactured by Applied Biosystems). After the synthesis, the solid phase support, with which the DNA oligonucleotide was bound, was immersed in a 30% aqueous ammonia/ethanol (3:1) mixed solution at 55° C. for 15 hr to cleave the DNA oligonucleotide from the solid phase support.

Comparative Example 3

Synthesis of 20-Mer DNA Using Support for Solid Phase Synthesis Bound with DMT-dT-3'-Succinate A solid phase support (10.4 mg) bound with DMT-dT-3'-succinate produced in Comparative Example 2 was packed in a reaction column and, in the same manner as in Example 4, 20-mer DNA oligonucleotide (5'-ATA CCG ATT AAG CGA AGT TT-3': SEQ ID NO: 1) was synthesized by DMT-on (synthesis scale 1 μmol). After the synthesis, the DNA oligonucleotide was cleaved from the solid phase support.

Experimental Example 3

Figure 3:
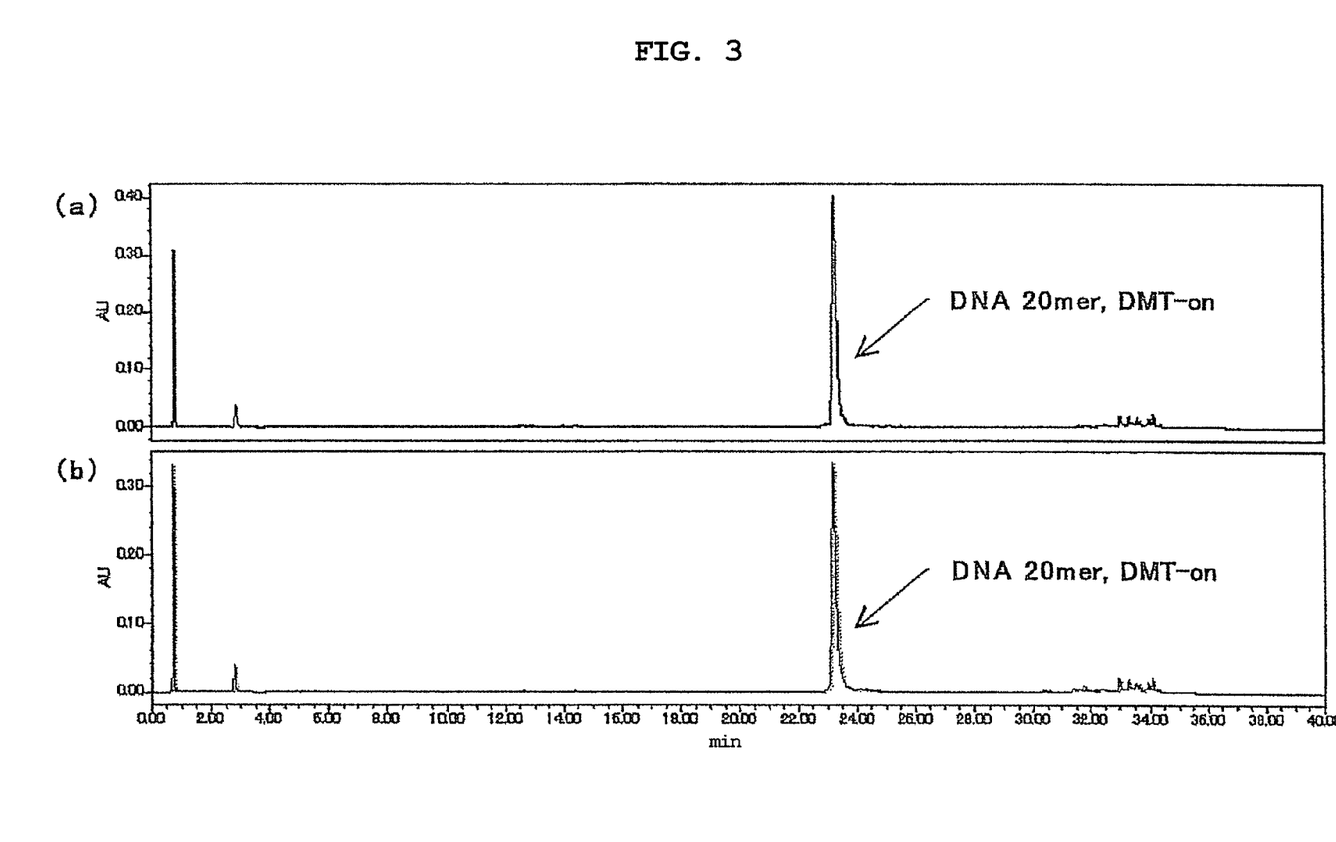
FIG. 3 shows HPLC chart of the DNA oligonucleotide solutions obtained in Example 6 (a) and Comparative Example 3 (b).

The DNA oligonucleotide solutions obtained in Example 6 and Comparative Example 3 were measured by HPLC. The measurement conditions were column; XBridge OST C18 2.5 μm 50×4.6 mm (manufactured by Waters), UV detection; 260 nm, Buffer A; 100 mM HFIP/7 mM TEA/water (pH 8.0), Buffer B; methanol, temperature: 30° C. FIGS. 3(a) and (b) show each HPLC chart.

```
SEQUENCE LISTING

<160> NUMBER OF SEQ ID NOS: 1

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
ataccgatta agcgaagttt                                                 20
```

As a result, the main peak of the DNA oligonucleotide produced in Example 6 was confirmed to be a 20-mer DNA oligonucleotide having a hydroxy group at the 3' terminal, since the detection time was the same as in Example 2. On the other hand, the main peak of the DNA oligonucleotide produced in Comparative Example 3 was also confirmed to be a 20-mer DNA oligonucleotide having a hydroxy group at the 3' terminal, since the detection time was the same as in Comparative Example 1.

Table 1 collectively shows the data obtained in Experimental Examples 1 to 3.

TABLE 1

| | solid phase support | sequence | molecular weight |
|---|---|---|---|
| Experimental Example 1 | Example 2 | (A) DNA 20mer (SEQ ID: NO 1) DMT-on | 6439 (found) |
| | Comparative Example 1 | DMT-dT-3'- succinate | 6439 (found) |
| Experimental Example 2 | Example 4 | (B) | 6439 (estimate) |
| | Comparative Example 2 | DMT-dT-3'- succinate | 6439 (estimate) |
| Experimental Example 3 | Example 6 | (C) | 6439 (estimate) |
| | Comparative Example 3 | DMT-dT-3'- succinate | 6439 (estimate) |

INDUSTRIAL APPLICABILITY

With the development of nucleic acid pharmaceutical products in recent years, the development of a more efficient and more functional method for synthesizing nucleic acid has been desired. The solid phase support for nucleic acid synthesis of the present invention can be used for, in addition to general nucleic acid synthesis, the synthesis of a nucleic acid having various modified sites. Moreover, a nucleic acid having a hydroxy group at the 3' terminal, which is automatically synthesized using the solid phase support for nucleic acid synthesis of the present invention, can be widely used irrespective of the kind of the nucleic acid medicament such as antisense, aptamer, siRNA and the like.

This application is based on a patent application No. 2012-016895 filed in Japan (filing date: Jan. 30, 2012), the contents of which are incorporated in full herein by this reference.

SEQUENCE LISTING FREE TEXT

SEQ ID NO: 1: artificially synthesized oligo 20-mers

The invention claimed is:

1. A linker for nucleic acid solid phase synthesis, comprising a compound represented by the following formula wherein
$X^1$ and $X^2$ are each independently a hydroxy-protecting group that is dissociated by acid,
$L^1$ and $L^2$ are each independently a linkage moiety that is cleaved by alkali,
$R^1$-$R^6$ are each independently a hydrogen atom; a $C_{1-6}$ alkyl group optionally substituted by a $C_{1-6}$ alkoxy group; a $C_{1-6}$ alkoxy group; a $C_{1-7}$ acyl group; a mono or di-$C_{1-6}$ alkylamino group; or a halogen atom, or
$R^2$ and $R^3$ are joined to form, together with the carbon atom bonded thereto, a 3- to 8-membered carbocycle or heterocycle each optionally substituted by a substituent selected from (1) an oxo group, (2) a $C_{1-6}$ alkyl group optionally substituted by a $C_{1-6}$ alkoxy group, and (3) a phenyl group optionally substituted by a $C_{1-6}$ alkoxycarbonyl group.

2. The linker according to claim 1, wherein at least one of $L^1$ and $L^2$ can be linked to a support for nucleic acid solid phase synthesis.

3. The linker according to claim 1, wherein $X^1$ and $X^2$ are dimethoxytrityl groups.

4. A support for nucleic acid solid phase synthesis, which has a structure represented by the following formula or wherein
$X^1$ and $X^2$ are each independently a hydroxy-protecting group that is dissociated by acid,
$L^1$ and $L^2$ are each independently a linkage moiety that is cleaved by alkali,
Sp is a solid phase support,
$R^1$-$R^6$ are each independently a hydrogen atom; a $C_{1-6}$ alkyl group optionally substituted by a $C_{1-6}$ alkoxy group; a $C_{1-6}$ alkoxy group; a $C_{1-7}$ acyl group; a mono or di-$C_{1-6}$ alkylamino group; or a halogen atom, or
$R^2$ and $R^5$ are joined to form, together with the carbon atom bonded thereto, a 3- to 8-membered carbocycle or heterocycle each optionally substituted by a substituent selected from (1) an oxo group, (2) a $C_{1-6}$ alkyl group optionally substituted by a $C_{1-6}$ alkoxy group, and (3) a phenyl group optionally substituted by a $C_{1-6}$ alkoxycarbonyl group.

5. The support according to claim 4, wherein $L^1$ is a succinyl group.

6. The support according to claim 4, wherein $L^1$ and $L^2$ are succinyl groups.

7. The support according to claim 6, wherein $X^1$ and $X^2$ are dimethoxytrityl groups.

8. The support of according to claim 7, wherein Sp is a solid phase support comprised of porous synthetic polymer particles or porous glass particles.

9. A method of producing a nucleic acid, comprising a step of performing a nucleic acid synthesis reaction on the support according to claim 4.

10. The production method according to claim 9, wherein the nucleic acid synthesis reaction is performed by a solid phase phosphoramidite method.

11. The linker according to claim 2, wherein $X^1$ and $X^2$ are dimethoxytrityl groups.

12. The support according to claim 4, wherein $X^1$ and $X^2$ are dimethoxytrityl groups.

13. The support of according to claim 12, wherein Sp is a solid phase support comprised of porous synthetic polymer particles or porous glass particles.

14. The support according to claim 5, wherein $X^1$ and $X^2$ are dimethoxytrityl groups.

15. The support according to claim 14, wherein Sp is a solid phase support comprised of porous synthetic polymer particles or porous glass particles.

16. The support of according to claim 4, wherein Sp is a solid phase support comprised of porous synthetic polymer particles or porous glass particles.

17. The support of according to claim 5, wherein Sp is a solid phase support comprised of porous synthetic polymer particles or porous glass particles.

18. The support of according to claim 6, wherein Sp is a solid phase support comprised of porous synthetic polymer particles or porous glass particles.

19. A method of producing a nucleic acid, comprising a step of performing a nucleic acid synthesis reaction on the support according to claim 8.

20. The production method according to claim 19, wherein the nucleic acid synthesis reaction is performed by a solid phase phosphoramidite method.

* * * * *